(12) United States Patent
Gao et al.

(10) Patent No.: US 11,535,601 B2
(45) Date of Patent: Dec. 27, 2022

(54) METHOD FOR PREPARING HEXAHYDROFURO-FURANOL DERIVATIVE, INTERMEDIATE THEREOF AND PREPARATION METHOD THEREOF

(71) Applicant: Jiangsu Ruike Medical Science And Technology Co., Ltd., Jiangsu (CN)

(72) Inventors: Zhaobo Gao, Zhejiang (CN); Jianhua Chen, Zhejiang (CN); Zhidong Wan, Zhejiang (CN); Dawei He, Zhejiang (CN); Zengle Zhou, Zhejiang (CN); Xiaodong Ma, Zhejiang (CN); Wei Xiang, Zhejiang (CN); Jingxin Lin, Zhejiang (CN); Yijiang Mei, Zhejiang (CN)

(73) Assignee: Jiangsu Ruike Medical Science And Technology Co., Ltd.

(*) Notice: Subject to any disclaimer, the term of this patent is extended or adjusted under 35 U.S.C. 154(b) by 0 days.

(21) Appl. No.: 16/975,894

(22) PCT Filed: Jul. 30, 2018

(86) PCT No.: PCT/CN2018/097733
§ 371 (c)(1),
(2) Date: Aug. 26, 2020

(87) PCT Pub. No.: WO2019/174176
PCT Pub. Date: Sep. 19, 2019

(65) Prior Publication Data
US 2021/0009544 A1    Jan. 14, 2021

(30) Foreign Application Priority Data
Mar. 16, 2018 (CN) .......................... 201810220506.1

(51) Int. Cl.
| C07D 307/33 | (2006.01) |
| C07D 493/04 | (2006.01) |
| C12P 17/04 | (2006.01) |
| C12P 17/16 | (2006.01) |

(52) U.S. Cl.
CPC ......... C07D 307/33 (2013.01); C07D 493/04 (2013.01); C12P 17/04 (2013.01); C12P 17/162 (2013.01); C07B 2200/07 (2013.01); C12Y 101/01 (2013.01)

(58) Field of Classification Search
None
See application file for complete search history.

(56) References Cited

U.S. PATENT DOCUMENTS

| 2004/0249175 A1 | 12/2004 | Kesteleyn et al. |
| 2007/0208184 A1 | 9/2007 | Quaedflieg et al. |
| 2011/0082297 A1 | 4/2011 | Wang et al. |
| 2014/0206655 A1 | 7/2014 | DeLuca et al. |

FOREIGN PATENT DOCUMENTS

| CN | 1938316 A | 3/2007 |
| CN | 100519561 C | 7/2009 |
| CN | 100537575 C | 9/2009 |
| CN | 103864813 A | 6/2014 |
| CN | 103896886 A | 7/2014 |
| EP | 2634180 A1 | 9/2013 |
| EP | 3778553 A1 | 2/2021 |
| JP | 2004107315 A | 4/2004 |
| JP | 2016509601 A | 3/2016 |
| JP | 2016210815 A | 12/2016 |

OTHER PUBLICATIONS

Blast ("Global Alignment Results for RID-UF5KJJRU 114" Run on Dec. 1, 2021, aligning Seq ID: 1 and Seq ID 11 of EP2634180, blast.ncbi.nlm.nih.gov/Blast.cgi) . (Year: 2021).*
International Search Report for Application No. PCT/CN2018/097733 dated Dec. 3, 2018, 3 pages.
Search Report for European Application No. 18909498.0 dated Oct. 26, 2021. 2 pgs.

* cited by examiner

Primary Examiner — Robert J Yamasaki
Assistant Examiner — Charles Zoltan Constantine
(74) Attorney, Agent, or Firm — Lerner, David, Littenberg, Krumholz & Mentlik, LLP

(57) ABSTRACT

The invention relates to the field of pharmaceutical synthesis, in particular to a preparation method of (3R,3aS,6aR)-hexahydrofuro[2,3-b]furan-3-ol derivatives and their intermediates. The preparation method is carried out starting from compound Formula A1.

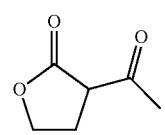

A1

In the preparation of (3R,3aS,6aR)-hexahydrofuro[2,3-b]furan-3-ol derivatives, the chirality was constructed by enzymatic method, and the products were prepared with high optical purity. The preparation method can be used to produce the key intermediates of (3R,3aS,6aR)-hexahydrofuro[2,3-b]furan-3-ol of darunavir commercially, which is a very economical route suitable for industrial production.

5 Claims, No Drawings

Specification includes a Sequence Listing.

METHOD FOR PREPARING HEXAHYDROFURO-FURANOL DERIVATIVE, INTERMEDIATE THEREOF AND PREPARATION METHOD THEREOF

CROSS-REFERENCE TO RELATED APPLICATIONS

The present application is a national phase entry under 35 U.S.C. § 371 of International Application No. PCT/CN2018/097733 filed Jul. 30, 2018, which claims priority from Chinese Application No. 201810220506.1, filed Mar. 16, 2018, all of which are hereby incorporated herein by reference.

TECHNICAL FIELD

The invention relates to the field of organic synthesis in pharmaceutical industry, in particular to the preparation method of hexahydrofuro-furanol derivatives and their intermediates.

TECHNICAL BACKGROUND

The chemical name of the compounds having the following Z structure is (3R,3aS,6aR)-hexahydrofuro[2,3-b]furan-3-ol:

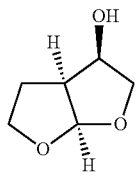

Z

It is one of the derivatives of hexahydrofuro[2,3-b]furan, meanwhile an intermediate of Darunavir as anti-HIV drug.

The Chinese patent with the application Ser. No. 02/817,639.1 (application date: 2002-9-6) and 200580010400.X. from Tibotec Pharmaceuticals Co., Ltd, provided the preparation method of (3R,3aS,6aR)-hexahydrofuro[2,3-b]furan-3-ol. The raw materials are the following compound Formula (3),

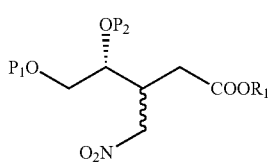

(3)

The compound Formula (3) was prepared from the starting material of Formula (1).

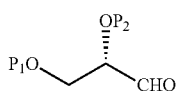

(1)

The Chinese patent with the application number 200380109926.4. from Sumitomo Chemical Co., Ltd provided the preparation method of above (3R,3aS,6aR)-hexahydrofuro[2,3-b]furan-3-ol. The raw materials are the following compound Formula (VIII),

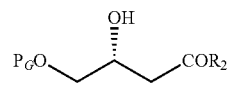

VIII

Sumitomo Chemical Co., Ltd. used chiral catalysts to generate chirality. However, the strategy wasn't applicable for commercial scale production.

European patent application EP2634180A1 (application date: 2012-1-3) by Lonza Ltd. disclosed the reduction of a carbonyl group to the hydroxyl group by carbonyl reductase. The patent lists a number of commercially available enzymes for example YNL331C from *Saccharomyces cerevisiae*. And mentioned that the compounds shown in Ia are suitable configurations.

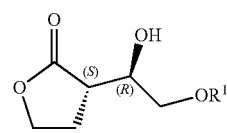

Ia

Considering that (3R,3aS,6aR)-hexahydrofuro[2,3-b]furan-3-ol is a key intermediate in the preparation of darunavir, it is necessary to develop more advantageous methods for the preparation of this key intermediate. This method can not only obtain the key intermediates with high yield and high de value, but also has low cost, mild reaction conditions and is suitable for industrialization.

Invention Content

The preparation method of (3R,3aS,6aR)-hexahydrofuro[2,3-b]furan-3-ol of the invention starts from the selection of starting material and the construction of chiral configuration. The starting material and the enzyamatic method to build chirality of the key intermediate is novel comparing with all the previous arts, with low cost and mild reaction conditions suitable for industrialization.

In order to achieve the technical purpose of the invention, the invention provides the following technical scheme:

First, the invention provides an intermediate preparation method of (3R,3aS,6aR)-hexahydrofuro[2,3-b]furan-3-ol. The chiral was constructed from compound Formula (B) or compound Formula (b-2) by enzymatic reduction reaction.

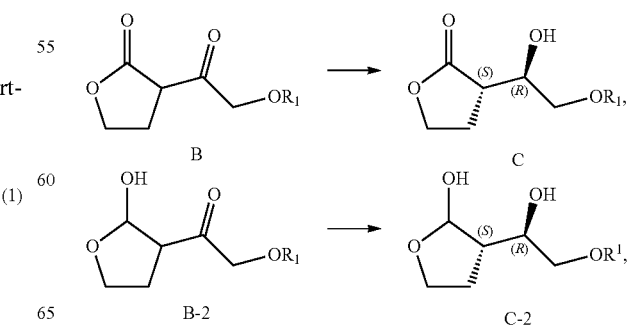

Wherein $R_1$ is hydrogen or protecting group of hydroxyl group;

The enzyme is a biological enzyme, such as aldehyde/ketone reductase, which is derived from the *Saccharomyces kudriavzevii* strain. Its amino acid sequence is the protein shown in SEQ ID NO: 1, or the protein with aldehyde/ketone reductase activity after the substitution, deletion or addition of one or more amino acid residues by SEQ ID NO: 1, or the protein with more than 80% homology with aldehyde/ketone reductase activity with the amino acid sequence shown in SEQ ID NO: 1. Its nucleotide sequence is shown in the sequence table with SEQ ID NO: 2. The aldehyde/ketone reductases could be derived from entire cells of genetically engineered bacteria, enzyme breaking fluid, freeze-dried powder, or from immobilized enzymes or from immobilized cells.

The feeding amount of the enzyme is 50-100 g/L, and the reaction temperature is 25-37° C.

The coenzyme, which is NADP+ or NADPH, could be selectively added to the enzymatic reduction reaction.

Glucose dehydrogenase could be selectively added to the enzymatic reduction reaction.

The enzymatic reduction reaction takes place in the presence of a solvent, which is a mixed solvent consisting of water or buffer solution and organic solvent.

The buffer solution is selected from one or more of the phosphate buffer solution, carbonate buffer solution, Tri-HCl buffer solution, citrate buffer solution or MOPS buffer solution.

The organic solvent is selected from one or more of DMSO, ethyl acetate, butyl acetate, isopropanol, DMF, TBME, dichloromethane and vinyl acetate.

Hplc-Ms and HPLC are used to monitor the bioconversion process of enzymatic reduction reaction of the invention until the substrate is fully utilized.

Further, the preparation method of an intermediates of (3R,3aS,6aR)-hexahydrofuro[2,3-b]furan-3-ol is constructed by enzymatic reduction reaction of compound Formula B, and further the hydroxyl group is protected by protective group.

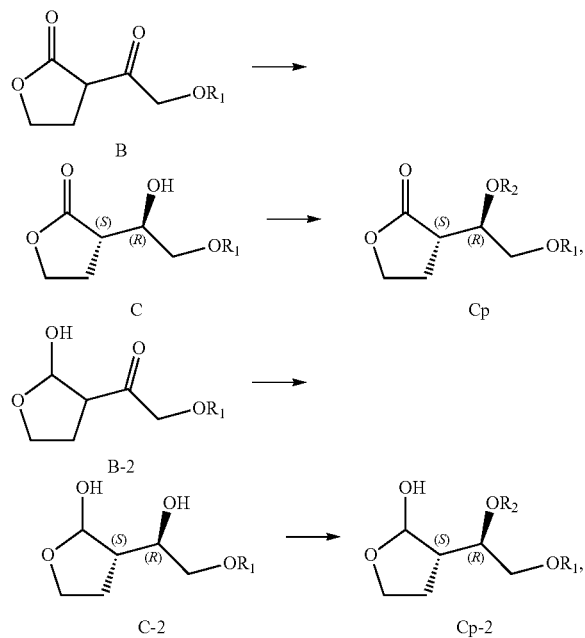

Wherein, $R_1$ is defined as above, $R_2$ is a protective group of hydroxyl, and the enzyme is the same as above.

In the above preparation method, the $R_1$ group is preferably a straight chain or branched acyl of $C_{2-11}$ benzoyl group or a mono-substituted or multi-substituted benzoyl group on the benzene ring, and the mono-substituted or multi-substituted group is alkyl group, alkoxy group, nitro group or cyano group.

On the other hand, the invention provides a preparation method of (3R,3aS,6aR)-hexahydrofuro[2,3-b]furan-3-ol, which is prepared by further reduction and ring-closing reaction of the intermediate compound C.

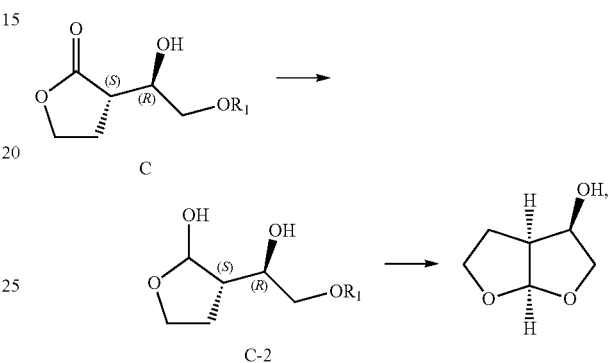

Wherein the definition of $R_1$ is the same as above.

The invention provides a preparation method of (3R,3aS,6aR)-hexahydrofuro[2,3-b]furan-3-ol, which may also be prepared by further reduction and ring-closing reaction of the intermediate compound Cp.

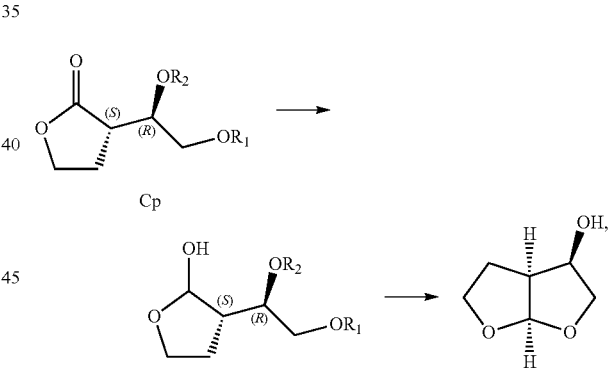

Wherein the definition of $R_1$ and $R_2$ are the same as above.

The invention provides a preparation method of (3R,3aS,6aR)-hexahydrofuro[2,3-b]furan-3-ol, which may be prepared by ring-closing reaction after the selective separation of the prepared compounds Formula C-2 or Formula Cp-2.

The compound Formula B is prepared by acylation of compound Formula A2, and the reaction is shown as follows:

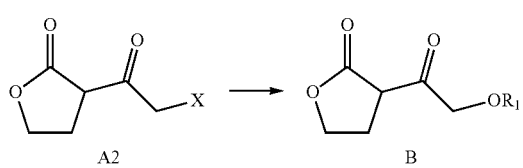

Wherein the $R_1$ is a straight chain or branched acyl benzoyl group of $C_{2-11}$ or a mono-substituted or multi-substituted benzoyl group on the benzene ring, and the mono-substituted or multi-substituted group is alkyl group, alkoxy group, nitro group or cyano group.

The compound A2 of the invention is prepared by halogenation of compound A1, and the reaction is shown as follows:

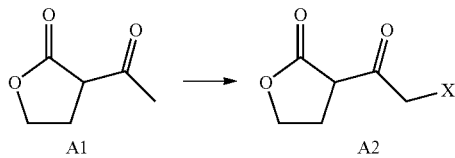

Wherein X is halogen.

The invention discloses a preparation method of (3R,3 aS,6aR)-hexahydrofuro[2,3-b]furan-3-ol, and the preferred embodiment is: preparation by halogenation reaction, acylation reaction, enzymatic reduction reaction, further reduction and ring-closing reaction.

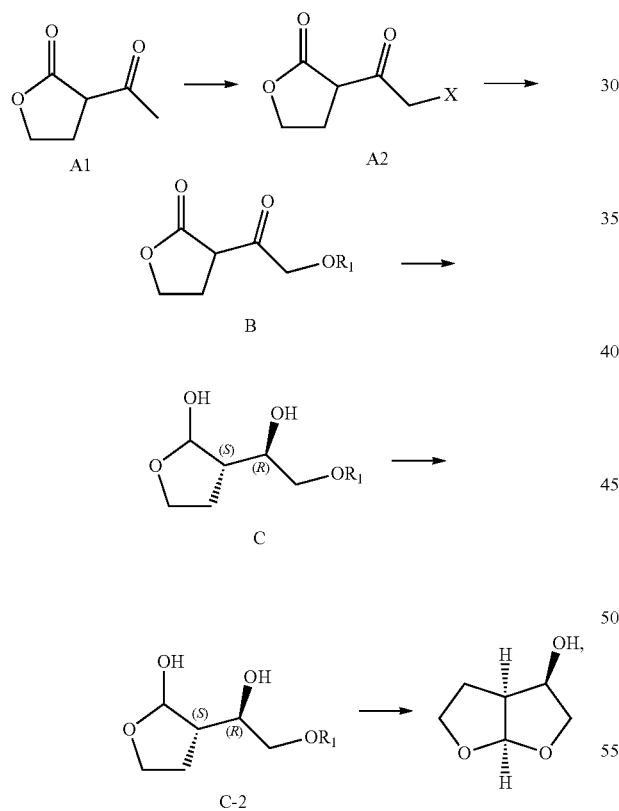

Wherein X is halogen, the definition of $R_1$ and enzyme are the same as above.

The invention discloses a preparation method of (3R,3 aS,6aR)-hexahydrofuro[2,3-b]furan-3-ol, and another preferred embodiment is: preparation by halogenation reaction, acylation reaction, enzymatic reduction reaction, protective reaction of hydroxyl group, further reduction and ring-closing reaction.

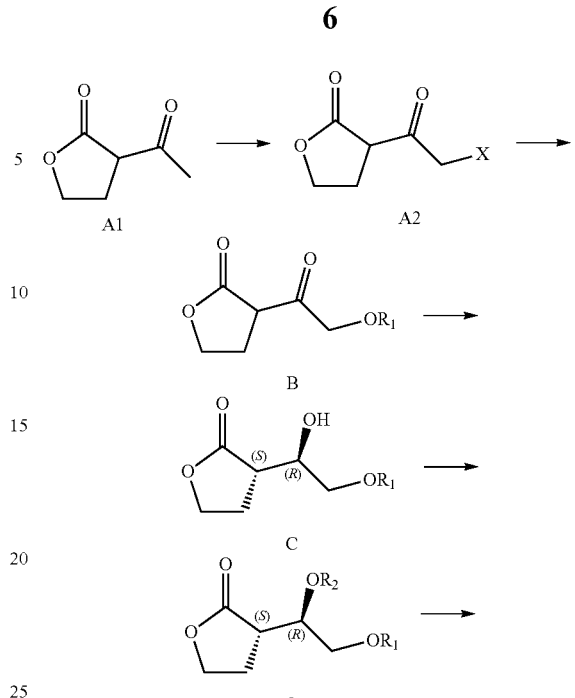

Wherein X is the halogen, the definition of $R_1$ is the same as that in claim 1, and the definition of $R_2$ is the same as that in claim 2; The definition of the enzyme is the same as above.

In the present invention, the compounds with chiral centers constructed by enzymatic method are protected and provide the intermediate compound of (3R,3 aS,6aR)-hexahydrofuro[2,3-b]furan-3-ol with the following structural formula:

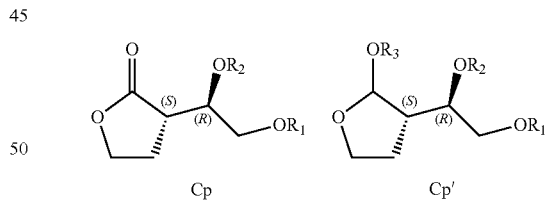

Wherein $R_1$ and $R_3$ are hydrogen or hydroxyl protective groups and $R_2$ are hydroxyl protective groups. The hydroxyl protective groups are alkyl, silyl, acyl of $C_{2-11}$, ring alkenyl of $C_{4-9}$, aryl, aralkyl, aroyl, phenyl and substituted phenyl. The silyl is tetramethyl-silyl, trimethyl-silyl, triethyl-silyl, tri-butyl silyl and tert-butyl dimethyl silyl. The alkyl is alkyl of $C_1$-$C_8$. The aromatic groups are phenyl, furan, thiophenyl or indole group. The substituted phenyl group is alkyl substituted phenyl group, alkoxy alkyl substituted phenyl group, nitro alkyl substituted phenyl group or halogen substituted phenyl group. The alkyl substituted phenyl is benzyl, diphenyl methyl and triphenyl methyl group; The phenyl substituted by the alkoxy alkyl group is p-methoxybenzyl; The substituted phenyl group of the nitro alkyl group is p-nitro benzyl group; The phenyl substituted by the halogen is p-chlorophenyl group.

The hydroxyl protective group is preferably benzoyl, mono-substituted or multi-substituted benzoyl on benzene ring, tert-butyl or benzyl.

The reduction reaction relates to a method of reducing another carbonyl group to a hemiketal product, and the reaction is shown as following:

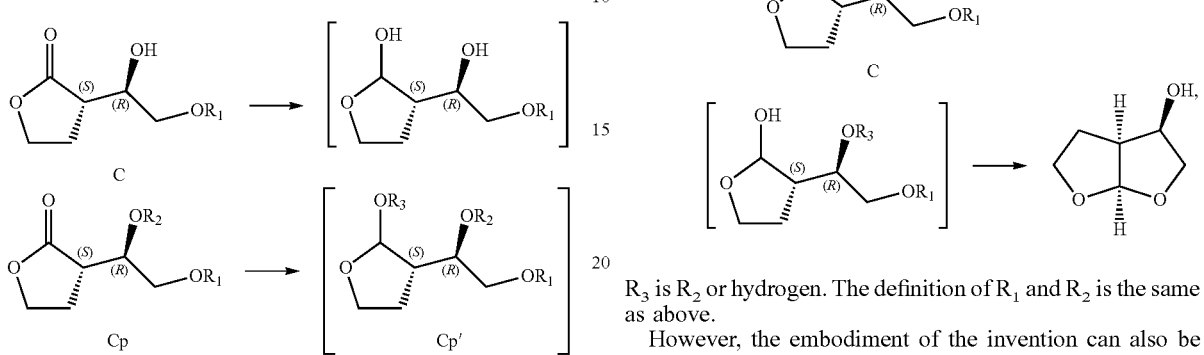

The above two reactions can be directly expressed as:

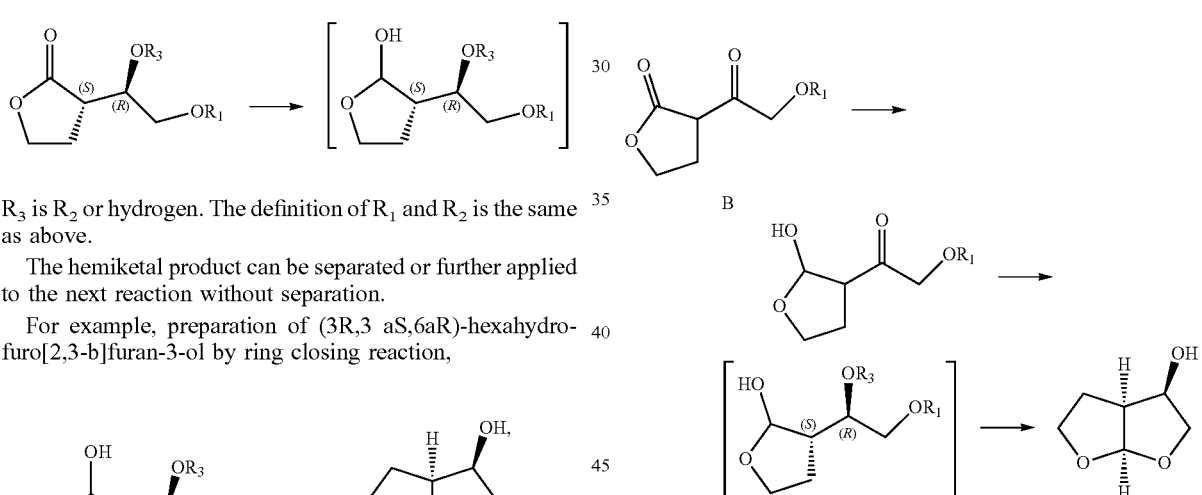

$R_3$ is $R_2$ or hydrogen. The definition of $R_1$ and $R_2$ is the same as above.

The hemiketal product can be separated or further applied to the next reaction without separation.

For example, preparation of (3R,3 aS,6aR)-hexahydrofuro[2,3-b]furan-3-ol by ring closing reaction,

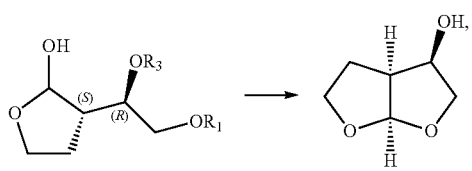

$R_3$ is $R_2$ or hydrogen. The definition of $R_1$ and $R_2$ is the same as above.

The reducing agent used for the reduction reaction to hemiacetal may be boron reducing agent, aluminum reducing agent or lithium silicon reducing agent. For example, sodium borohydride, sodium cyano-borohydride, lithium tetrahydroaluminum, Red-A1, lithium aluminum hydride, aluminum diisobutylhydride, lithium diisopropylamide and lithium hexamethyldisilazide.

The reagent for the ring-closing reaction is the common acid or base in the field.

The preferred embodiment of the invention is to construct the chiral center first, then selectively protect the hydroxyl group, then reduce it to the hemiketal product, and conduct the ring-closing reaction to prepare (3R,3 aS,6aR)-hexahydrofuro[2,3-b]furan-3-ol,

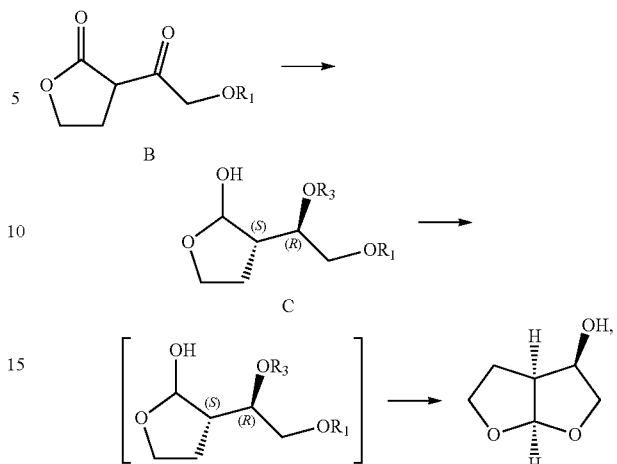

$R_3$ is $R_2$ or hydrogen. The definition of $R_1$ and $R_2$ is the same as above.

However, the embodiment of the invention can also be reduced to the hemiketal product first, and then the chiral center can be constructed. After selective separation, the ring-closing reaction can be carried out to prepare (3R,3 aS,6aR)-hexahydrofuro[2,3-b]furan-3-ol.

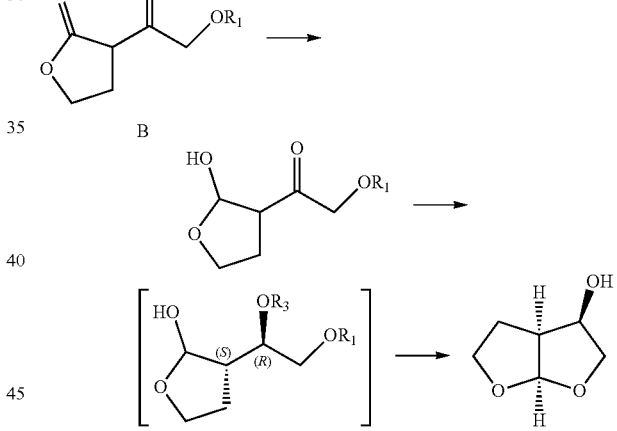

$R_3$ is $R_2$ or H. he definition of $R_1$ and $R_2$ is the same as above.

In the above acylation reaction of the invention,

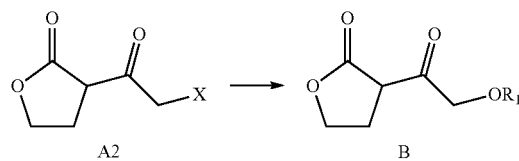

The $R_1$ group is preferably a straight chain or branched acyl benzoyl group of $C_{2-11}$ or a mono-substituted or multi-substituted benzoyl group on benzene ring.

The acylation reagent is a substitute benzoic acid compound or its salt, and the substituents of the substituted benzoic acid compound may be alkyl group, alkoxy group, nitro group or cyano group, etc. The substitutions may be mono-substitutions or multi-substitutions.

The acylation reaction may include addition of a base, which may be an organic base or an inorganic base, such as triethylamine, sodium carbonate, potassium carbonate, sodium bicarbonate, etc.

The $R_1$ is another substituent group, such as tert-butyl group. It can be transformed by the compound Formula A3 or by the compound Formula A2 reacting with tert-butyric acid, the compound Formula A3 was prepared by the compound Formula A2,

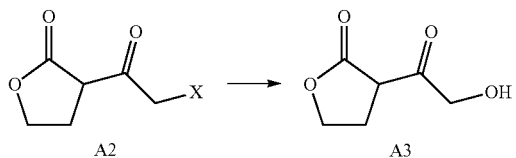

The above compounds Formula A2 are prepared by halogenation of compound A1, and the reaction formula is shown as follows:

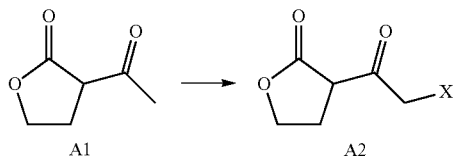

Wherein X is halogen.

In the invention, the reagent used in the halogenation reaction is hydrogen halide acid, etc The (3R,3aS,6aR)-hexahydrofuro[2,3-b]furan-3-ol preparation method of the invention can also be prepared by halogenation reaction, enzymatic reduction reaction, acylation reaction, ring-closing reaction after reduction, the reaction is shown as following:

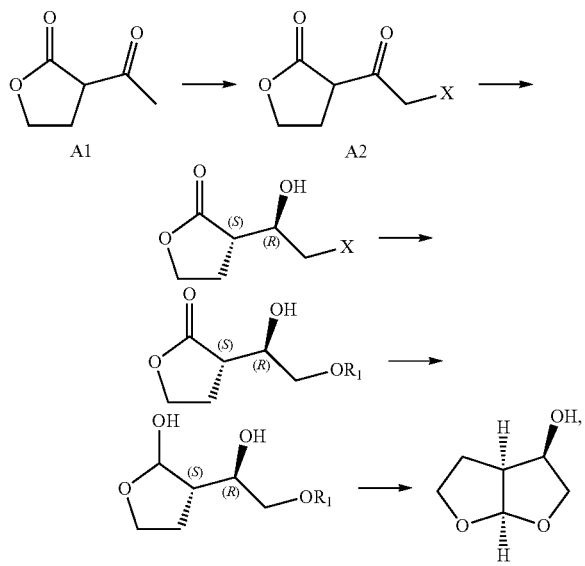

Wherein X is halogen, the definition of $R_1$ is the same as above.

The preparation method of (3R,3 aS,6aR)-hexahydrofuro[2,3-b]furan-3-ol provided by the invention adopts the enzymatic method to construct chirality, which can produce the product with high yield and high optical purity. Although prior method such as the European application above has disclosed carbonyl reductase polypeptides or microorganisms containing carbonyl reductase polypeptides achieve the reduction of carbonyl groups to hydroxyl groups, the enzymes used in the invention have more significant advantages, which are reflected in the preparation of products with higher optical purity and more suitable reaction conditions. The preparation method of (3R,3 aS,6aR)-hexahydrofuro[2, 3-b]furan-3-ol of the invention is suitable for industrial production.

EXAMPLES

In order to further understand the invention, the following is a detailed description of the preparation method, the intermediate and the preparation method of the (3R,3aS, 6aR)-hexahydrofuro[2,3-b]furan-3-ol derivatives provided by the invention. It is to be understood that these embodiment descriptions are intended only to further specify the characteristics of the invention and not to limit the scope of the invention or the scope of the claim to the invention.

Example 1

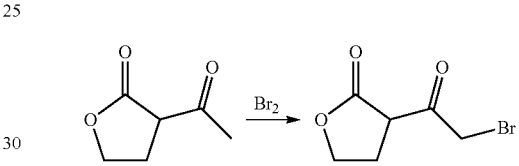

Compound A1, dichloromethane, was added to the reaction bottle and cooled down. Bromide was weighed and diluted with dichloromethane. The diluted bromide was transferred to a drop hopper and slowly added to control the internal temperature. After dripping, keep the internal temperature of reaction constant. Add water, control temperature and separate. The organic phase is put into another reaction bottle, water is added, and the liquid is extracted and separated. The organic phase was put into another reaction bottle, and 5% $NaHCO_3$ aqueous solution was added to extract and separate the liquid. The organic phase was put into another reaction bottle, and the upper aqueous phase was combined to add dichloromethane, which was extracted and separated. The abandoned water phase is combined with the organic phase, water is added, extracted, separated, abandoned water phase and the lower organic phase are concentrated in the rotary evaporator until no solvent is discharged, the yield is 90-95%.

Example 2

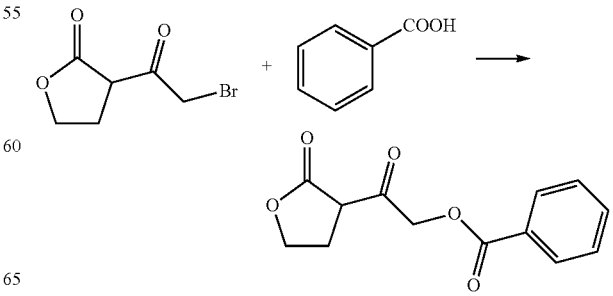

Add acetone, compound A2(X is bromine), benzoic acid to the reaction bottle, stirring and cooling. Add the triethylamine to the drop tank and start slowly to control the internal temperature. After dripping, heat up to room temperature and stir the reaction. After the reaction, filtration was performed. After filtration, filtrate was transferred to the distillation bottle for vacuum distillation. The temperature was controlled at 50-60° C. until the distillation bottle appeared solid paste. Supplying the distillation flask with ethyl acetate, stir well to dissolve, will shift the distillation of material liquid reaction in a bottle, the response of saturated salt water washing in the bottle, let stand, fluid, combined water layer, add the ethyl acetate extraction, let stand, layer, abandon water layer, combination of organic layer, anhydrous sodium sulfate was added to the organic layer stir to drying and suction filter. The filtrate was transferred to the reaction bottle for vacuum distillation, and the temperature was controlled at 50-60° C. until the reaction liquid turned into a solid paste. Then part of ethyl acetate was added and stirred to reflow to dissolve. The temperature was controlled at 50-60° C. Added n-heptane to the add tank. After cooling down slowly, keep stirring, filtration, drying target solid crude product, yield 70-75%.

Example 3

Entire—Cell Preparation of Aldehyde/Ketone Reductase Gene—Engineered Bacteria
Recombinant aldehyde/ketone reductase gene engineering bacteria, the preparation method is: The aldehyde/ketone reductase gene sequence from *Saccharomyces kudriavzevii* was selected for artificial design. The artificially designed sequence was synthesized by entire gene synthesis (commissioned by GenScript co., LTD.), and cloned into the Nde I and Xho I cleavage sites of the expression vector pET28a to transform host bacteria *E. coli* BL21 (DE3) competent cells. After the positive inverters were selected and identified by sequencing, the recombinant expression was obtained. Recombinant expression vector was transferred into *E. coli* BL21 (DE3) to obtain recombinant aldehyde/ketone reductase gene engineering bacteria that could induce expression of recombinant aldehyde/ketone reductase.

The recombinant aldehyde/ketone reductase gene engineering bacteria were inoculated into LB medium containing kanamycin and cultured overnight at 37° C. to obtain the seed culture medium. The seed medium was inoculated with 1% of the volume of the medium containing kanamycin. Then, it was cultured at 37° C. for 2-5 h, and induced by sterile IPTG, so that the final concentration of IPTG reached 0.1 mM. Then, it was incubated at 25° C. for 20 h. Finally, entire cells of *Saccharomyces kudriavzevii* aldehyde/ketone reductase gene were obtained by high speed centrifugation. The entire cells of the genetically engineered bacteria were broken by ultrasonic method to obtain the enzyme solution of the entire cells of the genetically engineered bacteria from *Saccharomyces* kudriavzevii. Aldehyde/ketone reductase is a protein whose amino acid sequence is SEQ ID NO: 1, and the nucleotide sequence of aldosterone reductase gene is shown in the sequence table SEQ ID NO: 2.

After induction, there were obvious protein bands at 45 kDa, indicating that aldehyde/ketone reductase was highly expressed in recombinant bacteria. The enzyme activity of aldehyde/ketone reductase pure protein was measured in a reaction system of 0.25 ml, including Tris-hcl, NADPH (pH 8.0, 2 mmol/L), 0.1 mmol/L substrate

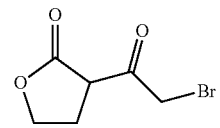

and appropriate enzymes. The reduction in absorbance at 340 nm was measured. The enzyme activity unit (U) was defined as the enzyme required to catalyze the oxidation of 1umol NADPH per minute under the above conditions.

The results showed that the aldehyde/ketone reductase activity of the recombinant gene-engineered aldehyde/ketone reductase was increased by more than 20% compared with that of the European patented (EP2634180A1) sequence, and by more than 50% compared with that of the unmutated aldehyde/ketone reductase sequence.

The aldehyde/ketone reductase gene engineering bacteria used in the embodiments of the invention are prepared by this method.

The glucose dehydrogenase used in the embodiment of the invention and in the control experiments are commercial enzymes purchased from sigma-aldrich.

The algorithm of ee value is shown as follows:

$$ee(\text{syn})=([R,R]-[S,S])/([R,R]+[S,S])$$

$$ee(\text{anti})=([R,S]-[S,R])/([R,S][S,R])$$

$$de=\{([R,S]+[S,R])-([R,R]+[S,S])\}/\{([R,S]+[S,R])+([R,R]+[S,S])\}$$

Enzymatic Reduction Reaction:

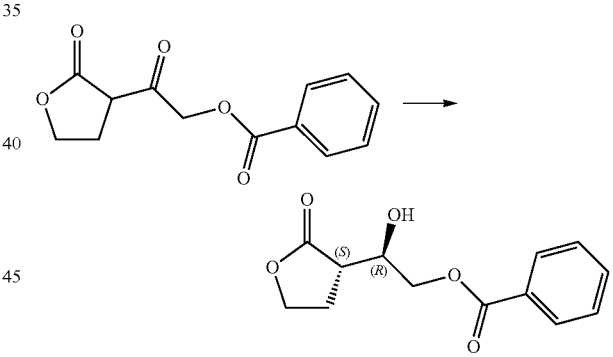

Step 1: the reaction was carried out in 1 L flask, the reaction system was controlled as 300 mL, and 260 mL of sterilized potassium phosphorus buffer solution was used to suspended aldehyde/ketone reductase gene-engineered bacteria entire cell crushing enzyme solution in the flask. Glucose dehydrogenase was put in, and cells was broken by ultrasound for 50 min. And then adding 25 g of glucose, 0.42 g of NADP+, and then weighing 8 g of the reactant, and dissolving it in 40 mL of DMSO. The demilitarized DMSO solution with substrates was slowly poured into the shaking bottle, and after 2 h of the reaction, 12 g of glucose was added to the solution. The entire cell volume of aldehyde/ketone gene engineering bacteria was 75 g/L, and the input volume of glucose dehydrogenase was 25 mg/L. The temperature is 37° C.; The conversion reaction was carried out in a shaker, whose rotating speed was controlled at 200 r/min, and the conversion time was 12 h. The conversion rate of the target product was 97.8%.

Step 2: The conversion liquid of the target product obtained in step 1 was purified. Add a constant volume of ethyl acetate to the reaction system, then extract at 37° C. for 15 min, repeat for 3 times, collect the ethyl acetate layer by centrifugation, add 5% anhydrous magnesium sulfate to the collected ethyl acetate layer and shake for 15 min, then filter to remove magnesium sulfate. Then the dehydrated ethyl acetate layer was concentrated at high temperature and reduced pressure, and the target product was 7.41 g, with a de value of 96.2% and an ee (anti) value of 99.5%.

Example 4

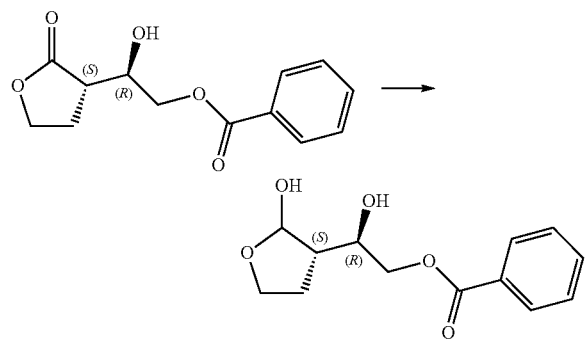

Adding compound B with a solid form (R₁ is benzoyl) (20.00 g) to a 500 ml dry clean four-neck round bottle, then toluene was added, the reaction was stirred. Vacuum replacement under nitrogen protection and cooling under nitrogen protection. Toluene was added to the constant pressure drop funnel under nitrogen protection. 70% Red-Al solution (26.50 g, 26.00 ml) was added to the constant pressure drop funnel under nitrogen protection. When the reaction solution cool to −15~−10° C., drop Red-Al solution, control the temperature, after dripping to keep temperature. Add pure water and ethyl acetate to the four-neck round bottle of 1000 ml in turn. Add sulfuric acid to the four four-neck round bottle of 1000 ml in the stirring state, cool them down and keep them warm. Drop the reaction liquid into the sulfuric acid solution. Control the solution at 0~10° C., after dripping to add ethyl acetate to stir. Add 10% sodium bicarbonate solution to the clean 1000 ml four-neck round bottle, cool it down, stop stirring, the reaction liquid was layered statically, and the upper organic layer was transferred to 10% sodium bicarbonate solution for stirring. Lower water layer was added the ethyl acetate to extract, stand for layered, then water layer was abandoned. Secondary ethyl acetate layer together into 10% sodium bicarbonate in aqueous solution was mixed. Then stir, control the temperature and layered. The alkaline water layer was added the ethyl acetate to extract, stir and control the temperature. Treatment of the caustic wash organic layer of pure water with washing stir, control the temperature and layered. The water layer with ethyl acetate to continue to extract, stand for layered, abandon the water layer, combine the organic phase. Added sodium sulfate to dry, filtration of the suction, evaporation of ethyl acetate, giving 17 g of product, yield of 84.33%.

Example 5

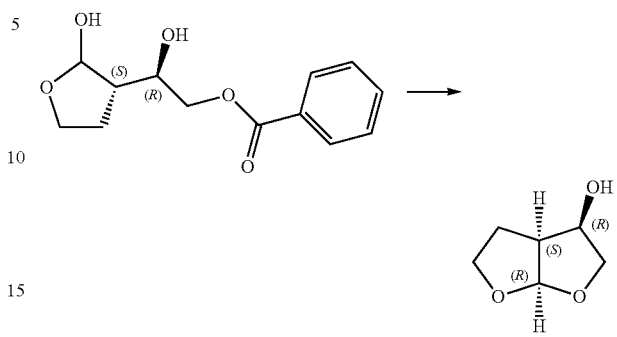

Methanol (10.00 ml) and compound C (R₁ is benzoyl) (1.00 g) were added to the reaction bottle in turn. The reaction solution was cooled to −15~−5° C., and sodium hydroxide solution (10.00 ml) was dropped. After the addition, the mixture was kept at a constant temperature and stirred until the reaction was complete. Then 10% sulfuric acid solution (4.00 g) was added. After the dripping, the reaction continued for keeping temperature, and then saturated sodium carbonate solution was added to adjust the pH. After the reaction solution was heated and decompressed by distillation to remove methanol, methyl tert-butyl ether was added to extract the organic layer, and then sodium chloride was added. Then the water layer was extracted by dichloromethane. The water layer was separated for recovery, and the organic layer was reduced by vacuum distillation to remove dichloromethane. The product was obtained for 0.38 g and the yield was 73.77%.

Example 6

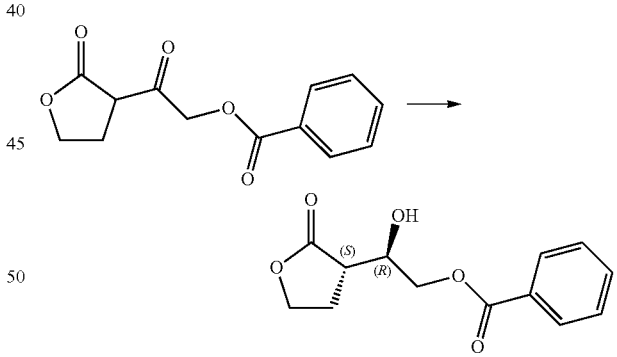

The preparation of the enzyme is the same as in example 3.

Step 1: the reaction was carried out in 5 L flask, the reaction system was controlled as 2 L, and 1.7 L of sterilized potassium phosphorus buffer solution was used to suspended aldehyde/ketone reductase gene-engineered bacteria entire cell in the flask. Glucose dehydrogenase was put in, and cells was broken by ultrasound for 50 min. And then adding 25 g of glucose, 0.42 g of NADP+, and then weighing 80 g of the reactant, and dissolving it in 300 mL of DMSO. The demilitarized DMSO solution with substrates was slowly poured into the shaking bottle, and after 2 h of the reaction, 12 g of glucose was added to the solution. The entire cell volume of aldehyde/ketone gene engineering bacteria was 75 g/L, and the input volume of glucose dehydrogenase was 25 mg/L. The temperature is 37° C.; The conversion reaction was carried out in a shaker, whose rotating speed was controlled at 200 r/min, and the conversion time was 12 h. The conversion rate of the target product was 97.8%.

Step 2: Purification of product from step 1 which contain intermediate compound of formula VIII. Purification steps refer to example 3. The target product was 77.1 g, with a de value of 95.3% and an ee(anti) value of 99.6%.

Example 7

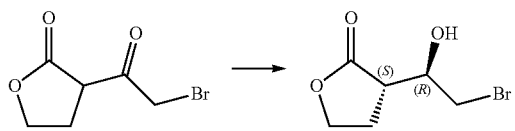

Step 1: the reaction was carried out in 1 L flask, the reaction system was controlled as 300 mL, and 250 mL of deionized water was used to suspended aldehyde/ketone reductase gene-engineered bacteria entire cell in the flask. glucose dehydrogenase was put in, And then adding 10 ml of glucose(2.5 mol/L), 0.26 g of NADP+, and then weighing 10 g of the reactant, and dissolving it in 30 mL of butyl acetate. The butyl acetate solution with substrates was slowly poured into the shaking bottle, and after 1 h of the reaction, 10 mL of glucose (2.5 mol/L) was added to the solution. The entire cell volume of aldehyde/ketone gene engineering bacteria was 75 g/L, and the input volume of glucose dehydrogenase was 25 mg/L. The temperature is 37° C.; The conversion reaction was carried out in a shaker, whose rotating speed was controlled at 200 r/min, and the conversion time was 12 h. The conversion rate of the target product was 97.8%.

Step 2: The conversion liquid of the target product obtained in step 1 was purified. Add a constant volume of ethyl acetate to the reaction system, then extract at 37° C. for 15 min, repeat for 3 times, collect the ethyl acetate layer by centrifugation, add 5% anhydrous magnesium sulfate to the collected ethyl acetate layer and shake for 15 min, then filter to remove magnesium sulfate. Then the dehydrated ethyl acetate layer was concentrated at high temperature and reduced pressure, and the target product was 9.55 g, with a de value of 99.1% and an ee(anti) value of 99.7%. 1H NMR (600 MHz, CDCl₃) δ 2.269~2.301 (m, 1H, J=6 Hz), 2.367~2.404 (m, 1H), 2.954~2.993 (m, 1H, J=6 Hz), 3.438~3.466 (m, 1H), 3.520~3.549 (m, 1H), 4.227~4.269 (m, 1H), 4.298 4.326 (m, 1H), 4.391~4.420 (m, 1H). MS(ESI): m/z 210.03 [M+H]⁺

Example 8

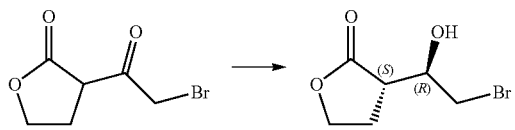

Step 1: the reaction was carried out in 5 L flask, the reaction system was controlled as 2 L, and 1.5 L of deionized water was used to suspended aldehyde/ketone gene-engineered bacteria entire cell in the flask. glucose dehydrogenase was put in, And then adding 10 ml of glucose(2.5 mol/L), 3 g of NADP+, and then weighing 100 g of the reactant, and dissolving it in 300 mL of butyl acetate. The butyl acetate solution with substrates was slowly poured into the shaking bottle, and after 1 h of the reaction, 100 mL of glucose (2.5 mol/L) was added to the solution. The entire cell volume of aldehyde/ketone gene engineering bacteria was 100 g/L, and the input volume of glucose dehydrogenase was 25 mg/L. The temperature is 28° C.; The conversion reaction was carried out in a shaker, whose rotating speed was controlled at 200 r/min, and the conversion time was 12 h. The conversion rate of the target product was 97.8%.

Step 2: Purification of product from step 1 which contain intermediate compound of Formula VIII. Purification steps refer to example 3. The target product was 9.42 g, with a de value of 96.9% and an ee(anti) value of 99.4%.

Example 9

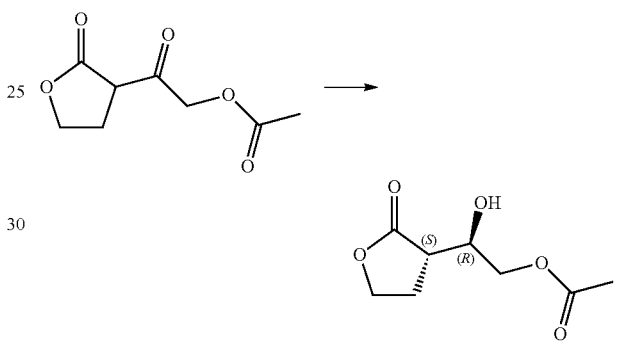

Step 1: the reaction was carried out in 1 L flask, the reaction system was controlled as 300 mL, and 250 mL of deionized water was used to suspended aldehyde/ketone reductase gene-engineered bacteria entire in the flask. glucose dehydrogenase was put in, And then adding 10 ml of glucose(2.5 mol/L),0.26 g of NADP+, and then weighing 10 g of the reactant, and dissolving it in 30 mL of butyl acetate. The butyl acetate solution with substrates was slowly poured into the shaking bottle, and after 1 h of the reaction, 10 mL of glucose (2.5 mol/L) was added to the solution. The entire cell volume of aldehyde/ketone gene engineering bacteria was 75 g/L, and the input volume of glucose dehydrogenase was 25 mg/L. The temperature is 37° C.; The conversion reaction was carried out in a shaker, whose rotating speed was controlled at 200 r/min, and the conversion time was 12 h. The conversion rate of the target product was 97.8%.

Step 2: Purification of product from step 1 which contain intermediate compound of Formula VIII. Purification steps refer to example 3. The target product was 9.37 g, with a de value of 97.1% and an ee(anti) value of 99.5%.

Example 10

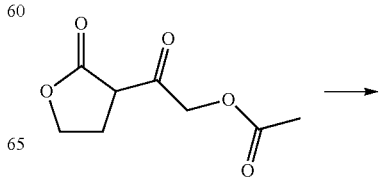

-continued

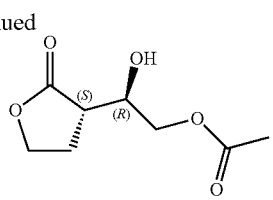

Step 1: the reaction was carried out in 5 L flask, the reaction system was controlled as 2 L, and 1.6 L of deionized water was used to suspended aldehyde/ketone reductase gene-engineered bacteria entire cell in the flask. glucose dehydrogenase was put in, And then adding 100 ml of glucose(2.5 mol/L),0.25 g of NADP+, and then weighing 100 g of the reactant, and dissolving it in 200 mL of butyl acetate. The butyl acetate solution with substrates was slowly poured into the shaking bottle, and after 1 h of the reaction, 100 mL of glucose (2.5 mol/L) was added to the solution. The entire cell volume of aldehyde/ketone gene engineering bacteria was 50 g/L, and the input volume of glucose dehydrogenase was 25 mg/L. The temperature is 25° C.; The conversion reaction was carried out in a shaker, whose rotating speed was controlled at 200 r/min, and the conversion time was 12 h. The conversion rate of the target product was 97.8%.

Step 2: Purification of product from step 1 which contain intermediate compound of Formula VIII. Purification steps refer to example 3. The target product was 93.1 g, with a de value of 95.6% and an ee(anti) value of 99.6%.

Example 11: Control Experiment

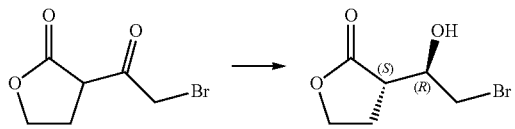

Step 1: the reaction was carried out in 1 L flask, the reaction system was controlled as 300 mL, and 250 mL of deionized water was used to suspended aldehyde/ketone reductase gene-engineered bacteria entire cell in the flask. The encoding sequence of aldehyde/ketone reductase gene used in the entire cell of the engineered bacteria is as shown in the sequence published in EP2634180 of the European patent (SEQ ID NO 12 in EP2634180 of the patent). The sequence was synthesized by total gene synthesis (commissioned by GenScript Co., Ltd.). Preparation steps refer to example 3. glucose dehydrogenase was put in, And then adding 10 ml of glucose(2.5 mol/L),0.26 g of NADP+, and then weighing 10 g of the reactant, and dissolving it in 30 mL of butyl acetate. The butyl acetate solution with substrates was slowly poured into the shaking bottle, and after 1 h of the reaction, 10 mL of glucose (2.5 mol/L) was added to the solution. The entire cell volume of aldehyde/ketone gene engineering bacteria was 75 g/L, and the input volume of glucose dehydrogenase was 25 mg/L. The temperature is 37° C.; The conversion reaction was carried out in a shaker, whose rotating speed was controlled at 200 r/min, and the conversion time was 12 h.

Step 2: Purification steps refer to example 3. The target product was 8.11 g, with a de value of 85.1% and an ee(anti) value of 93.3%.

Example 12: Control Experiment

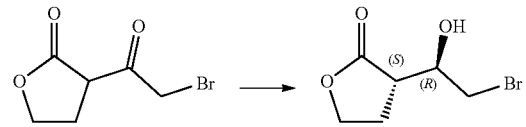

Step 1: the reaction was carried out in 1 L flask, the reaction system was controlled as 300 mL, and 250 mL of deionized water was used to suspended aldehyde/ketone reductase gene-engineered bacteria entire cell of *Saccharomyces kudriavzevii* in the flask. The encoding sequence of aldehyde/ketone reductase gene used in the entire cell of the engineered bacteria is as shown in the sequence published in SEQ ID NO 3. (The coding sequence of aldehyde/ketone reductase gene has not been artificially designed) The sequence was synthesized by total gene synthesis (commissioned by GenScript Co., Ltd.). Preparation steps refer to example 3. glucose dehydrogenase was put in, And then adding 10 ml of glucose(2.5 mol/L),0.26 g of NADP+, and then weighing 10 g of the reactant, and dissolving it in 30 mL of butyl acetate. The butyl acetate solution with substrates was slowly poured into the shaking bottle, and after 1 h of the reaction, 10 mL of glucose (2.5 mol/L) was added to the solution. The entire cell volume of aldehyde/ketone gene engineering bacteria was 75 g/L, and the input volume of glucose dehydrogenase was 25 mg/L. The temperature is 37° C.; The conversion reaction was carried out in a shaker, whose rotating speed was controlled at 200 r/min, and the conversion time was 12 h.

Step 2: Purification steps refer to example 3. The target product was 7.73 g, with a de value of 79.6% and an ee(anti) value of 88.7%.

```
Nucleotide Sequence Table
Serial number of SEQ ID NO 1 are:
Met Ser Asp Leu Phe Lys Pro Ala Pro Glu Pro Pro Thr Glu Leu Gly Arg Leu Arg Val Leu Ser Lys Thr Ala Gly Ile Arg Val Ser Pro Leu Ile Leu Gly Gly Ala Ser Ile Gly Asp Ala Trp Ser Gly Phe Met Gly Ser Met Asn Lys Glu Gln Ala Phe Glu Leu Leu Asp Ala Phe Tyr Glu Ala Gly Gly Asn Cys Val Asp Thr Ala Asn Ser Tyr Gln Asn Glu Glu Ser Glu Ile Trp Ile Gly Glu Trp Met Lys Ser Arg Lys Leu Arg Asp Gln Ile Val Ile Ala Thr Lys Phe Thr Gly Asp Tyr Lys Lys Tyr Glu
```

-continued

Val Gly Gly Gly Lys Ser Ala Asn Tyr Cys Gly Asn His Lys His Ser

Leu His Val Ser Val Arg Asp Ser Leu Arg Lys Leu Gln Thr Asp Trp

Ile Asp Ile Leu Tyr Val His Trp Trp Asp Tyr Met Ser Ser Ile Glu

Glu Val Met Asp Ser Leu His Ile Leu Ile Gln Gln Gly Lys Val Leu

Tyr Leu Gly Val Ser Asp Thr Pro Ala Trp Val Ser Ala Ala Asn

Asn Tyr Ala Thr Ser His Gly Lys Thr Pro Phe Ser Ile Tyr Gln Gly

Lys Trp Asn Val Leu Asn Arg Asp Phe Glu Arg Asp Ile Ile Pro Met

Ala Arg His Phe Gly Met Ala Leu Ala Pro Trp Asp Val Met Gly Gly

Gly Lys Phe Gln Ser Lys Lys Ala Met Glu Glu Trp Lys Lys Asn Gly

Glu Gly Leu Arg Thr Ala Val Gly Gly Pro Glu Gln Thr Glu Leu Glu

Val Lys Ile Ser Glu Ala Leu Asn Lys Ile Ala Glu Glu His Gly Thr

Glu Ser Val Thr Ala Ile Ala Ile Ala Tyr Val Arg Ser Lys Ala Lys

Asn Val Phe Pro Leu Val Gly Gly Arg Lys Ile Glu His Leu Lys Gln

Asn Ile Glu Ala Leu Ser Ile Lys Leu Thr Pro Glu Gln Ile Glu Tyr

Leu Glu Ser Ile Val Thr Phe Asp Val Gly Phe Pro Lys Ser Asn Ile

Gly Asp Asp Pro Ala Val Thr Lys Lys Leu Ser Pro Leu Thr Ser Met

Ser Ala Arg Ile Ser Phe Asp Asn

Serial number of SEQ ID NO 2 are:
atgagcgatc tgtttaaacc ggcgccggaa ccgccgaccg aactgggccg cctgcgcgtg    60
ctgagcaaaa ccgcgggcat tcgcgtgagc ccgctgattc tgggcggcgc gagcattggc   120
gatgcgtgga cggctttat gggcagcatg aacaaagaac aggcgtttga actgctggat   180
gcgttttatg aagcgggcgg caactgcgtg ataccgcga cagctatca gaacgaagaa   240
agcgaaattt ggattggcga atggatgaaa agccgcaaac tgcgcgatca gattgtgatt   300
gcgaccaaat ttaccggcga ttataaaaaa tatgaagtgg cggcggcaa aagcgcgaac   360
tattgcggca accataaaca tagcctgcat gtgagcgtgc gcgatagcct gcgcaaactg   420
cagaccgatt ggattgatat tctgtatgtg cattggtggg attatatgag cagcattgaa   480
gaagtgatgg atagcctgca tattctgatt cagcagggca agtgctgta tctgggcgtg   540
agcgataccc cggcgtgggt ggtgagcgcg gcgaacaact atgcgaccag ccatggcaaa   600
accccgttta gcatttatca gggcaaatgg aacgtgctga ccgcgattt tgaacgcgat   660
attattccga tggcgcgcca ttttggcatg gcgctggcgc cgtgggatgt gatgggcggc   720
ggcaaatttc agagcaaaaa agcgatggaa gaatggaaaa aaacggcga aggcctgcgc   780
accgcggtgg gcgccccgga acagaccgaa ctggaagtga aaattagcga agcgctgaac   840
aaaattgcgg aagaacatgg caccgaaagc gtgaccgcga ttgcgattgc gtatgtgcgc   900
agcaaagcga aaacgtgtt ccgctggtg gcggccgca aattgaaca tctgaaacag   960
aacattgaag cgctgagcat taactgacc ccggaacaga ttgatatct ggaaagcatt  1020
gtgacctttg atgtgggctt tccgaaaagc aacattggcg atgatccggc ggtgaccaaa  1080
aaactgagcc cgctgaccag catgagcgcg cgcattagct ttgataacta a           1131

Serial number of SEQ ID NO 3 are:
atgtctgatg tatttggacc tgcacctgaa ccacctaccg agttaggacg tctaagagtt    60
ctctctaaaa cagctggtat aagagtctct ccgctaatat gggaggtat gtcgattggt   120
gacgcctggt caggattcat ggggtcaatg aacaaggagc gggcttttga gctgcttgat   180
gccuttteg aggcaggtgg aaacttcatt gatactgcaa ataattacca aaatgaacag   240

-continued

```
tcagaggcat ggataggtga atggatggtt tcaagaaaat tgcgtgacca aattgttatt  300
gccaccaaat tcaccacaga ctataagaag tatgaagtgg gcaagggcag aagtgccaac  360
ttctgtggta atcacaagca tagtttacac gtaagtgtga gagattctct tcgcaaattg  420
cagactgatt ggattgacat tctctatgtt cactggtggg attatatgag ttcgatcgag  480
gaagttatgg atagtctgca tattcttgtg cagcagggca aggtcctcta cctgggagta  540
tctgatacac ctgcatgggt cgtgtctgct gcaaattact acgctacctc tcacgggaaa  600
actcccttca gcatctatca aggtaaatgg aatctgttga atagggactt tgagcgtgaa  660
attattccaa tggctaggca ttttggtatg gctctcgctc catgggatgt catgggaggg  720
ggaagatttc agagcaaaaa agctttagaa gaacggaaga agagtggaga gggcctgcgt  780
agctttgttg gtacatctga acagacggat gcagaggtta agatcagcga ggcattgtcg  840
aaggttgctg aggaacatgg cattgagtct gtcacagcta ttgccattgc ctatgtccgc  900
tccaaagcga agcatgtttt cccattggtt ggaggaagga aaattgagca cctcaaacaa  960
aatattgagg cgttgagtat taaattgaca ccaggacaga tagaatatct agaaagcatt 1020
gtcccattcg atgttgggtt ccctagcaat ttcatcggag atgatcctgc agttactaag 1080
aaacttgcat tccttccagc aatgtctgcc aagattgctt ttgacgatta g        1131
```

---

The invention claimed is:

1. A method of preparation of an intermediate compound for the synthesis of (3R,3aS,6aR)-hexahydrofuro[2,3-b]furan-3-ol, comprising: enzymatically reducing a compound of formula (B) or a compound formula (B-2) to produce a compound of formula (C) or (C-2) respectively;

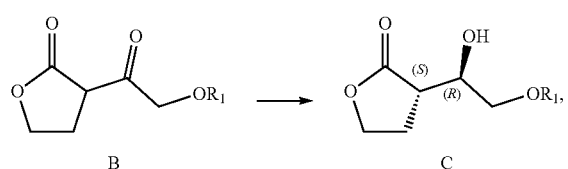

B → C

-continued

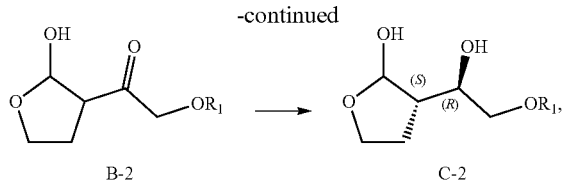

B-2 → C-2 wherein the enzyme is an aldehyde/ketone reductase having the amino acid sequence as shown in SEQ ID NO:1, or produced from the nucleotide sequence of the aldehyde/ketone reductase gene of SEQ ID NO: 2, and, wherein $R_1$ is a hydrogen or a linear or branched acyl group of $C_{2-11}$, a benzoyl group or a mono-substituted or multi-substituted benzoyl group on the benzene ring, and the mono-substituted or multi-substituted group is alkyl group, alkoxy group, nitro group or cyano group.

2. The method of claim 1, wherein the aldehyde/ketone reductase is in the form of a total cell of genetically engineered bacteria, a cell lysate, a freeze-dried powder or an immobilized enzyme or an immobilized cell.

3. The method of claim 2, further comprising adding the aldehyde/ketone reductase to a reaction mixture in the form of recombining whole cells in an amount of 10-100 g/L, and conducting the enzymatic reduction at a temperature of 25-37° C.

4. The method of claim 1, wherein the reaction takes place in the presence of a solvent.

5. The method of claim 4, wherein the solvent is a mixed solvent consisting of water or buffer solution and organic solvent;
- the buffer solution is selected from a group consisting of phosphate buffer solution, carbonate buffer solution, Tri-HCl buffer solution, citrate buffer solution and MOPS buffer solution;
- the organic solvent is selected from a group consisting of DMSO, ethyl acetate, butyl acetate, isopropanol, DMF, TBME, dichloromethane and vinyl acetate.

* * * * *

SEQUENCE LISTING

<160> NUMBER OF SEQ ID NOS: 3

<210> SEQ ID NO 1
<211> LENGTH: 376
<212> TYPE: PRT
<213> ORGANISM: artificial sequence
<220> FEATURE:
<223> OTHER INFORMATION: sequence is synthesized

<400> SEQUENCE: 1

```
Met Ser Asp Leu Phe Lys Pro Ala Pro Glu Pro Pro Thr Glu Leu Gly
1               5                   10                  15

Arg Leu Arg Val Leu Ser Lys Thr Ala Gly Ile Arg Val Ser Pro Leu
            20                  25                  30

Ile Leu Gly Gly Ala Ser Ile Gly Asp Ala Trp Ser Gly Phe Met Gly
        35                  40                  45

Ser Met Asn Lys Glu Gln Ala Phe Glu Leu Leu Asp Ala Phe Tyr Glu
    50                  55                  60

Ala Gly Gly Asn Cys Val Asp Thr Ala Asn Ser Tyr Gln Asn Glu Glu
65                  70                  75                  80

Ser Glu Ile Trp Ile Gly Glu Trp Met Lys Ser Arg Lys Leu Arg Asp
                85                  90                  95

Gln Ile Val Ile Ala Thr Lys Phe Thr Gly Asp Tyr Lys Lys Tyr Glu
            100                 105                 110

Val Gly Gly Gly Lys Ser Ala Asn Tyr Cys Gly Asn His Lys His Ser
        115                 120                 125

Leu His Val Ser Val Arg Asp Ser Leu Arg Lys Leu Gln Thr Asp Trp
    130                 135                 140

Ile Asp Ile Leu Tyr Val His Trp Trp Asp Tyr Met Ser Ser Ile Glu
145                 150                 155                 160

Glu Val Met Asp Ser Leu His Ile Leu Ile Gln Gln Gly Lys Val Leu
                165                 170                 175
```

```
Tyr Leu Gly Val Ser Asp Thr Pro Ala Trp Val Ser Ala Ala Asn
            180                 185                 190

Asn Tyr Ala Thr Ser His Gly Lys Thr Pro Phe Ser Ile Tyr Gln Gly
        195                 200                 205

Lys Trp Asn Val Leu Asn Arg Asp Phe Glu Arg Asp Ile Ile Pro Met
    210                 215                 220

Ala Arg His Phe Gly Met Ala Leu Ala Pro Trp Asp Val Met Gly Gly
225                 230                 235                 240

Gly Lys Phe Gln Ser Lys Lys Ala Met Glu Glu Trp Lys Lys Asn Gly
                245                 250                 255

Glu Gly Leu Arg Thr Ala Val Gly Gly Pro Glu Gln Thr Glu Leu Glu
            260                 265                 270

Val Lys Ile Ser Glu Ala Leu Asn Lys Ile Ala Glu Glu His Gly Thr
        275                 280                 285

Glu Ser Val Thr Ala Ile Ala Ile Ala Tyr Val Arg Ser Lys Ala Lys
    290                 295                 300

Asn Val Phe Pro Leu Val Gly Gly Arg Lys Ile Glu His Leu Lys Gln
305                 310                 315                 320

Asn Ile Glu Ala Leu Ser Ile Lys Leu Thr Pro Glu Gln Ile Glu Tyr
                325                 330                 335

Leu Glu Ser Ile Val Thr Phe Asp Val Gly Phe Pro Lys Ser Asn Ile
            340                 345                 350

Gly Asp Asp Pro Ala Val Thr Lys Lys Leu Ser Pro Leu Thr Ser Met
        355                 360                 365

Ser Ala Arg Ile Ser Phe Asp Asn
    370                 375

<210> SEQ ID NO 2
<211> LENGTH: 1131
<212> TYPE: DNA
<213> ORGANISM: artificial sequence
<220> FEATURE:
<223> OTHER INFORMATION: sequence is synthesized

<400> SEQUENCE: 2
atgagcgatc tgtttaaacc ggcgccggaa ccgccgaccg aactgggccg cctgcgcgtg      60
ctgagcaaaa ccgcgggcat tcgcgtgagc ccgctgattc tgggcggcgc gagcattggc     120
gatgcgtgga gcggctttat gggcagcatg aacaaagaac aggcgtttga actgctggat     180
gcgttttatg aagcgggcgg caactgcgtg gataccgcga acagctatca gaacgaagaa     240
agcgaaattt ggattggcga atggatgaaa agccgcaaac tgcgcgatca gattgtgatt     300
gcgaccaaat ttaccggcga ttataaaaaa tatgaagtgg cggcggcaa agcgcgaac       360 tattgcggca accataaaca tagcctgcat gtgagcgtgc gcgatagcct gcgcaaactg     420
cagaccgatt ggattgatat tctgtatgtg cattggtggg attatatgag cagcattgaa     480
gaagtgatgg atagcctgca tattctgatt cagcagggca aagtgctgta tctgggcgtg     540
agcgataccc cggcgtgggt ggtgagcgcg gcgaacaact atgcgaccag ccatggcaaa     600
accccgttta gcatttatca gggcaaatgg aacgtgctga ccgcgatttt tgaacgcgat     660
attattccga tggcgcgcca ttttggcatg gcgctggcgc cgtgggatgt gatgggcggc     720
ggcaaatttc agagcaaaaa agcgatggaa gaatggaaaa aaacggcga aggcctgcgc     780 accgcggtgg gcggcccgga acagaccgaa ctggaagtga aaattagcga agcgctgaac     840
aaaattgcgg aagaacatgg caccgaaagc gtgaccgcga ttgcgattgc gtatgtgcgc     900
```

```
agcaaagcga aaaacgtgtt tccgctggtg ggcggccgca aaattgaaca tctgaaacag    960
aacattgaag cgctgagcat taaactgacc ccggaacaga ttgaatatct ggaaagcatt   1020
gtgacctttg atgtgggctt tccgaaaagc aacattggcg atgatccggc ggtgaccaaa   1080
aaactgagcc cgctgaccag catgagcgcg cgcattagct ttgataacta a            1131
```

<210> SEQ ID NO 3
<211> LENGTH: 1131
<212> TYPE: DNA
<213> ORGANISM: artificial sequence
<220> FEATURE:
<223> OTHER INFORMATION: sequence is synthesized

<400> SEQUENCE: 3

```
atgtctgatg tatttggacc tgcacctgaa ccacctaccg agttaggacg tctaagagtt     60
ctctctaaaa cagctggtat aagagtctct ccgctaatat gggaggtat gtcgattggt    120 gacgcctggt caggattcat ggggtcaatg aacaaggagc gggcttttga gctgcttgat    180 gccttttcg aggcaggtgg aaacttcatt gatactgcaa ataattacca aaatgaacag    240
tcagaggcat ggataggtga atggatggtt tcaagaaaat tgcgtgacca aattgttatt    300
gccaccaaat tcaccacaga ctataagaag tatgaagtgg gcaagggcag aagtgccaac    360
ttctgtggta atcacaagca tagtttacac gtaagtgtga gagattctct tcgcaaattg    420
cagactgatt ggattgacat tctctatgtt cactggtggg attatatgag ttcgatcgag    480
gaagttatgg atagtctgca tattcttgtg cagcagggca aggtcctcta cctgggagta    540
tctgatacac ctgcatgggt cgtgtctgct gcaaattact acgctacctc tcacgggaaa    600
actcccttca gcatctatca aggtaaatgg aatctgttga atagggactt tgagcgtgaa    660
attattccaa tggctaggca ttttggtatg gctctcgctc catgggatgt catgggaggg    720
ggaagatttc agagcaaaaa agctttagaa gaacggaaga agagtggaga gggcctgcgt    780
agctttgttg gtacatctga acagacggat gcagaggtta agatcagcga ggcattgtcg    840
aaggttgctg aggaacatgg cattgagtct gtcacagcta ttgccattgc ctatgtccgc    900
tccaaagcga agcatgtttt cccattggtt ggaggaagga aaattgagca cctcaaacaa    960
aatattgagg cgttgagtat taaattgaca ccaggacaga tagaatatct agaaagcatt   1020
gtcccattcg atgtttgggtt ccctagcaat ttcatcggag atgatcctgc agttactaag   1080
aaacttgcat tccttccagc aatgtctgcc aagattgctt ttgacgatta g            1131
```